US00PP25819P2

(12) United States Plant Patent
Jacobs

(10) Patent No.: US PP25,819 P2
(45) Date of Patent: Aug. 18, 2015

(54) ***FREESIA* PLANT NAMED 'ZAFRETWEET'**

(50) Latin Name: *Freesia×hybrida*
Varietal Denomination: Zafretweet

(71) Applicant: Henricus Cornelius Maria Jacobs, Bleiswijk (NL)

(72) Inventor: Henricus Cornelius Maria Jacobs, Bleiswijk (NL)

(73) Assignee: Van Zanten Plants B.V., Rijsenhout (NL)

( * ) Notice: Subject to any disclaimer, the term of this patent is extended or adjusted under 35 U.S.C. 154(b) by 178 days.

(21) Appl. No.: 13/987,341

(22) Filed: Jul. 15, 2013

(51) Int. Cl.
*A01H 5/00* (2006.01)

(52) U.S. Cl.
USPC ..... Plt./299

(58) Field of Classification Search
USPC ..... Plt./299
See application file for complete search history.

*Primary Examiner* — Annette Para
(74) *Attorney, Agent, or Firm* — C. A. Whealy

(57) ABSTRACT

A new and distinct cultivar of *Freesia* plant named 'Zafretweet', characterized by its compact, upright, somewhat outwardly spreading and uniform plant habit; freely flowering habit; large intense yellow-colored flowers; and excellent container performance.

1 Drawing Sheet

Botanical designation: *Freesia×hybrida.*
Cultivar denomination: 'ZAFRETWEET'.

BACKGROUND OF THE INVENTION

The present invention relates to a new and distinct cultivar of *Freesia* plant, botanically known as *Freesia×hybrida*, commercially used as a potted *Freesia* plant and hereinafter referred to by the name 'Zafretweet'.

The new *Freesia* plant is a product of a planned breeding program conducted by the Inventor in Rijsenhout, The Netherlands. The objective of the breeding program is to create new compact *Freesia* plants with numerous large and attractive flowers.

The new *Freesia* plant originated from a cross-pollination made by the Inventor in Rijsenhout, The Netherlands in April, 2001 of a proprietary *Freesia×hybrida* selection identified as code number 95-3-1247P-01, not patented, as the female, or seed, parent with a proprietary *Freesia×hybrida* selection identified as code number 95-3-2607P02, not patented, as the male, or pollen, parent. The new *Freesia* plant was discovered and selected by the Inventor as a single flowering plant from within the progeny of the stated cross-pollination in a controlled greenhouse environment in Rijsenhout, The Netherlands in June, 2002.

Asexual reproduction of the new *Freesia* plant by corms and cormlets in a controlled greenhouse environment in Rijsenhout, The Netherlands since September, 2002 has shown that the unique features of this new *Freesia* plant are stable and reproduced true to type in successive generations.

SUMMARY OF THE INVENTION

Plants of the new *Freesia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Zafretweet'. These characteristics in combination distinguish 'Zafretweet' as a new and distinct potted *Freesia* plant:

1. Compact, upright, somewhat outwardly spreading and uniform plant habit.
2. Freely flowering habit.
3. Large intense yellow-colored flowers.
4. Excellent container performance.

Plants of the new *Freesia* differ primarily from plants of the female parent selection in flower color as plants of the female parent selection have darker yellow-colored flowers.

Plants of the new *Freesia* differ primarily from plants of the male parent selection in leaf size as plants of the new *Freesia* have shorter leaves than plants of the male parent selection.

Plants of the new *Freesia* can be compared to plants of *Freesia×hybrida* 'Vapopey', disclosed in U.S. Plant Pat. No. 9,293. In side-by-side comparisons conducted in Rijsenhout, The Netherlands, plants of the new *Freesia* differed primarily from plants of 'Vapopey' in the following characteristics:

1. Plants of the new *Freesia* were slightly taller than plants of 'Vapopey'.
2. Plants of the new *Freesia* had broader leaves than plants of 'Vapopey'.
3. Plants of the new *Freesia* were more freely flowering than plants of 'Vapopey'.
4. Plants of the new *Freesia* had larger flowers than plants of 'Vapopey'.
5. Plants of the new *Freesia* and 'Vapopey' differed slightly in flower color.

BRIEF DESCRIPTION OF THE PHOTOGRAPHS

The accompanying colored photographs illustrate the overall appearance of the new *Freesia* plant showing the colors as true as it is reasonably possible to obtain in colored reproductions of this type. Colors in the photographs may differ slightly from the color values cited in the detailed botanical description which accurately describe the colors of the new *Freesia* plant.

The photograph at the top of the sheet comprises a side perspective view of a typical flowering plant of 'Zafretweet' grown in a container.

The photograph at the bottom of the sheet is a close-up view of a typical flowering plant of 'Zafretweet'.

DETAILED BOTANICAL DESCRIPTION

The aforementioned photographs and following observations and measurements describe plants of the new *Freesia* grown during the spring with five corms per 13-cm containers in a glass-covered greenhouse in Rijsenhout, The Netherlands. During the production of the plants, day temperatures ranged from 14° C. to 24° C. and night temperatures ranged from 14° C. to 16° C. Plants were eleven weeks old when the photographs and the description were taken. In the following description, color references are made to The Royal Horticultural Society Colour Chart, 2007 Edition, except where general terms of ordinary dictionary significance are used.

Botanical classification: *Freesia×hybrida* 'Zafretweet'.

Parentage:

*Female, or seed, parent*.—Proprietary *Freesia×hybrida* selection identified as code number 95-3-1247P-01, not patented.

*Male or pollen parent*.—Proprietary *Freesia×hybrida* selection identified as code number 95-3-2607P02, not patented.

Propagation:

*Type*.—By corms and cormlets.

*Time to initiate roots, spring*.—About ten days at temperatures ranging from 14° to 24° C.

*Time to produce a rooted young plant, spring*.—About three weeks at temperatures ranging from 14° to 24° C.

*Root description*.—Thick, fleshy; close to 155A to 155D in color.

*Rooting habit*.—Low branching; sparse.

*Corms*.—Shape: Roughly spherical. Height: About 2.5 cm to 4 cm. Diameter: About 1.5 cm to 2.5 cm. Texture: Smooth, glossy. Color: Close to 155A.

Overall plant description:

*Plant and growth habit*.—Compact, upright, somewhat outwardly spreading and uniform plant habit; moderately vigorous growth habit.

*Plant height*.—About 38 cm to 40 cm.

*Plant diameter* (*spread*).—About 17 cm.

Lateral branch description:

*Aspect*.—Mostly upright and slightly curving.

*Length*.—About 14 cm.

*Diameter*.—About 2 mm.

*Strength*.—Strong.

*Texture*.—Smooth, glabrous.

*Color*.—Close to 144A.

Leaf description:

*Appearance*.—Simple, two-ranked; sessile.

*Length*.—About 25 cm to 35 cm.

*Width*.—About 2.5 cm to 4 cm.

*Shape*.—Elliptic to lanceolate.

*Apex*.—Acute.

*Base*.—Cuneate.

*Margin*.—Entire.

*Texture, upper and lower surfaces*.—Smooth, glabrous.

*Venation pattern*.—Parallel.

*Color*.—Developing and fully expanded leaves, upper surface: Close to 137C; venation, close to N137A. Developing and fully expanded leaves, lower surface: Close to 138B; venation, close to N137A.

Flower description:

*Flower type and habit*.—Single funnel-shaped flowers arranged on terminal spikes; flowers face mostly upright; perianth segments fused; freely flowering habit with 12 to 14 flowers per inflorescence.

*Natural flowering season*.—Flowering continuous during the spring in The Netherlands; early flowering habit, plants begin flowering about eleven weeks after planting.

*Fragrance*.—Present, sweet.

*Flower longevity on the plant*.—About one week; flowers persistent.

*Flower buds*.—Length: About 5 mm to 20 mm. Diameter: About 2 mm to 3 mm. Shape: Elliptic. Color: Close to 147B.

*Spike length*.—About 7 cm.

*Spike diameter*.—About 8 cm.

*Flower diameter*.—About 5.5 cm.

*Flower length*.—About 5 cm.

*Perianth*.—Arrangement: Six arranged in two whorls, each whorl with three segments fused towards the base. Inner perianth segments: Length: About 5.5 cm to 6 cm. Width: About 2.8 cm. Shape: Obovate. Apex: Rounded. Margin: Entire. Texture, upper and lower surfaces: Smooth, glabrous. Color, when opening, upper surface: Close to 11D; towards the margins, close to 12A. Color, when opening, lower surface: Close to 11D; towards the margins, close to 10C. Color, fully opening, upper surface: Close to 10B to 10C; center, close to 10C to 10D; and central spot, close to 21B. With development, colors becoming closer to 10D in the center; towards the margins, close to 15C; and central spot, close to 23A. Color, fully opened, lower surface: Close to 11D and towards the margins, close to 8A. With development, colors becoming closer to 11D and towards the margins, close to 14C. Outer perianth segments: Length: About 5.5 cm to 6 cm. Width: About 2.6 cm. Shape: Obovate. Apex: Rounded. Margin: Entire. Texture, upper and lower surfaces: Smooth, glabrous. Color, when opening and fully opened, upper surface: Close to 10A and 12B; central spot, close to 21B. Color, when opening and fully opened, lower surface: Close to 11D; towards the margins, close to 8A.

*Pedicels*.—Length: About 3 mm to 4 mm. Diameter: About 1 mm to 1.5 mm. Strength: Strong. Angle: About 30° to 90° from peduncle axis. Texture: Smooth, glabrous. Color: Close to 146C.

*Reproductive organs*.—Stamens: Quantity per flower: Typically three. Filament length: About 2.5 cm. Filament color: Close to 10C. Anther shape: Elliptic. Anther length: About 6 mm to 8 mm. Anther color: Close to 155D. Pollen amount: None observed. Pistils: Quantity per flower: One. Style length: About 3 cm. Style color: Close to 155A. Stigma shape: Six-parted. Stigma color: Close to 155A.

*Fruits and seeds*.—Fruit and seed development have not been observed on plants of the new *Freesia*.

Disease & pest resistance: Plants of the new *Freesia* have not been observed to be resistant to pathogens and pests common to *Freesia* plants.

Garden performance: Plants of the new *Freesia* have been observed to have excellent garden performance and to tolerate wind, rain and temperatures from about 4° C. to about 35° C.

It is claimed:

1. A new and distinct *Freesia* plant named 'Zafretweet' as illustrated and described.

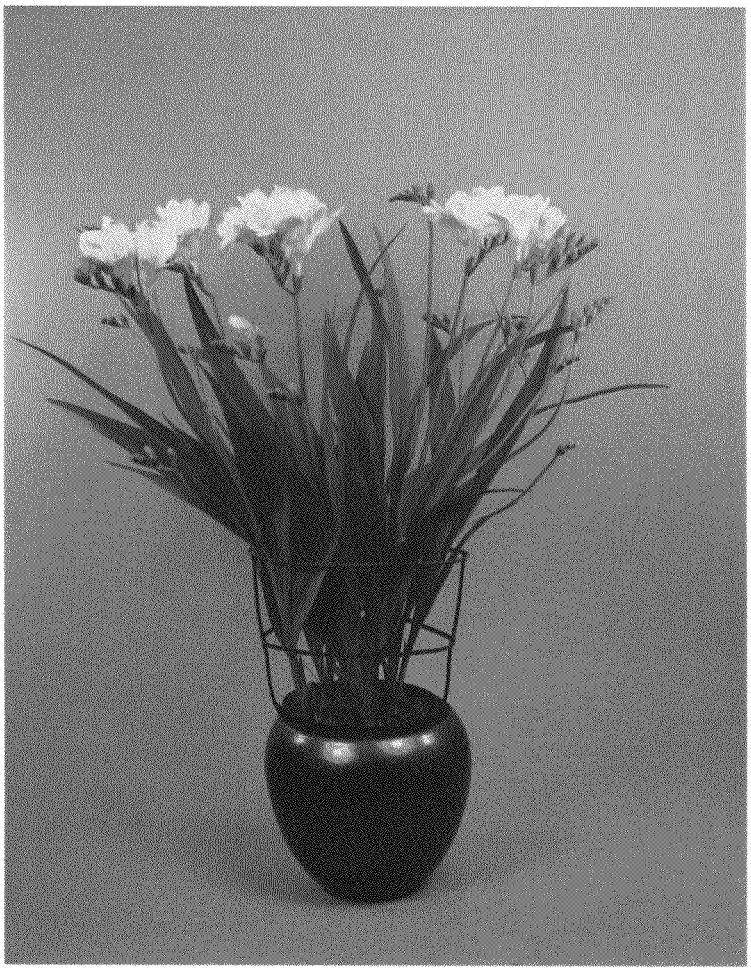
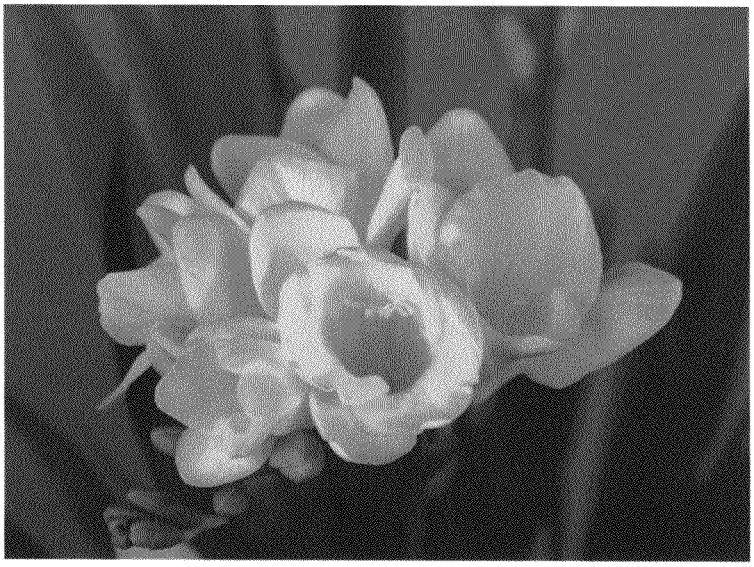

* * * * *